(12) United States Patent
Chaki et al.

(10) Patent No.: US 8,900,417 B2
(45) Date of Patent: Dec. 2, 2014

(54) PURIFICATION METHOD OF 2,3,3,3-TETRAFLUOROPROPENE

(75) Inventors: Takehiro Chaki, Settsu (JP); Kazuhiro Takahashi, Settsu (JP)

(73) Assignee: Daikin Industries, Ltd., Osaka (JP)

( * ) Notice: Subject to any disclaimer, the term of this patent is extended or adjusted under 35 U.S.C. 154(b) by 195 days.

(21) Appl. No.: 13/808,358

(22) PCT Filed: Jul. 21, 2011

(86) PCT No.: PCT/JP2011/067179
§ 371 (c)(1),
(2), (4) Date: Jan. 4, 2013

(87) PCT Pub. No.: WO2012/011609
PCT Pub. Date: Jan. 26, 2012

(65) Prior Publication Data
US 2013/0105296 A1    May 2, 2013

Related U.S. Application Data

(60) Provisional application No. 61/367,050, filed on Jul. 23, 2010.

(51) Int. Cl.
*C07C 17/386*   (2006.01)
*C01B 7/19*   (2006.01)
*C07C 17/38*   (2006.01)
*C07C 17/383*   (2006.01)

(52) U.S. Cl.
CPC ............. *C07C 17/386* (2013.01); *C01B 7/196* (2013.01); *C07C 17/38* (2013.01); *C07C 17/383* (2013.01)
USPC ................ 203/57; 203/60; 203/62; 203/63; 203/64; 203/66

(58) Field of Classification Search
USPC .......... 203/50, 51, 52, 56, 57, 60, 62, 63, 64, 203/66
See application file for complete search history.

(56) References Cited

U.S. PATENT DOCUMENTS

| 2,996,555 | A | 8/1961 | Rausch |
|---|---|---|---|
| 2007/0131535 | A1* | 6/2007 | Shiflett et al. .................... 203/50 |
| 2010/0308259 | A1* | 12/2010 | Knapp ..................... 252/182.12 |
| 2011/0257444 | A1* | 10/2011 | Knapp et al. .................. 570/175 |
| 2012/0305382 | A1* | 12/2012 | Knapp et al. .................... 203/67 |

FOREIGN PATENT DOCUMENTS

| WO | 2008/002499 | 1/2008 |
|---|---|---|
| WO | 2008/008519 | 1/2008 |
| WO | 2008/024508 | 2/2008 |
| WO | 2009/105512 | 8/2009 |

OTHER PUBLICATIONS

International Search Report issued Oct. 10, 2011 in International (PCT) Application No. PCT/JP2011/067179.
Written Opinion issued Oct. 10, 2011 in International (PCT) Application No. PCT/JP2011/067179.

\* cited by examiner

*Primary Examiner* — Nina Bhat
*Assistant Examiner* — Brandi M Doyle
(74) *Attorney, Agent, or Firm* — Wenderoth, Lind & Ponack, L.L.P.

(57) ABSTRACT

This invention provides a method for purifying HFO-1234yf by removing HF from a mixture of HFO-1234yf and HF under simple and economically advantageous conditions. According to the present invention, this is a purification method for 2,3,3,3-tetrafluoropropene, (1) the purification method comprising the step of subjecting a mixture comprising 2,3,3,3-tetrafluoropropene and hydrogen fluoride to extractive distillation in a distillation column A using an extractant, thereby obtaining a fraction I that contains 2,3,3, 3-tetrafluoropropene and has a lower ratio of hydrogen fluoride to 2,3,3,3-tetrafluoropropene than that of the mixture, while obtaining a fraction II that contains hydrogen fluoride and has a lower ratio of 2,3,3,3-tetrafluoropropene to hydrogen fluoride than that of the mixture; (2) the extractant comprising at least one member selected from the group consisting of: (i) alcohols represented by ROH, wherein R is a $C_{1-5}$ alkyl group, (ii) ethers represented by ROR', wherein R and R' are the same or different, and each is a $C_{1-4}$ alkyl group, (iii) fluorinated alcohols represented by RfOH, wherein Rf is a $C_{1-3}$ fluoroalkyl group, (iv) ketones represented by RCOR', wherein R and R' are the same or different, and each is a $C_{1-4}$ alkyl group, (v) esters represented by RCOOR', wherein R and R' are the same or different, and each is a $C_{1-4}$ alkyl group, (vi) polyols represented by R(OH)n, wherein R is a $C_{1-4}$ alkyl group, and n is an integer of 2 to 3, and (vii) ethylene glycols represented by $R^1O(CH_2CH_2O)_nR^2$, wherein $R^1$ and $R^2$ are the same or different, and each is hydrogen or a $C_{1-4}$ alkyl group, and n is an integer of 1 to 3.

20 Claims, 2 Drawing Sheets

PURIFICATION METHOD OF 2,3,3,3-TETRAFLUOROPROPENE

This application claims the benefit of U.S. Provisional Application No. 61/367,050, filed Jul. 23, 2010.

TECHNICAL FIELD

The present invention relates to a method for purifying 2,3,3,3-tetrafluoropropene ($CF_3CF=CH_2$, HFO-1234yf; hereinafter also referred to as "HFO-1234yf"). More specifically, the present invention relates to a method for purifying HFO-1234yf by removing HF from a mixture containing HFO-1234yf and hydrogen fluoride (HF).

BACKGROUND ART

There are various methods for producing HFO-1234yf, which shows great promise as a refrigerant for car air conditioners, etc., because of its low global warming potential (GWP). For example, PTL 1 discloses a production process in which HF in an amount exceeding the stoichiometrically required amount is supplied to a reaction starting raw material ($CCl_3CF_2CH_3$). Further, PTL 2 discloses a production process in which fluorocarbon ($CF_3CFHCFH_2$) is dehydrofluorinated. In these processes, the outflow from the reactor is a mixture of the desired product HFO-1234yf and HF present in an amount at least equimolar to that of HFO-1234yf.

To remove HF from a mixture of HFO-1234yf and HF in order to obtain a purified product of HFO-1234yf, the mixture of HFO-1234yf and HF is treated so that HF is absorbed by water or alkali, which is known as a general method for removing HF from a mixture of an organic substance and HF. However, this method requires a large quantity of water or alkali, leading to the discharge of a large amount of industrial waste. Thus, this method is not beneficial in terms of environmental preservation and production cost. In another generally known method for removing HF, $H_2SO_4$ is used to collect HF as a fluorosulfuric acid. In this method, however, the fluorosulfuric acid that is generated is highly corrosive, and the materials of equipment used are therefore limited to highly corrosion-resistant materials, leading to an increase in production cost. Furthermore, in this HF-removing method, reuse of the removed HF in the reaction (recycling use) requires a high level of technology, leading to an increase in production cost when the collected HF is either recycled or disposed.

The processes described below resolve these problems. For example, PTL 3 discloses a process in which a mixture of HFO-1234yf and HF is distilled, and an azeotropic mixture of HFO-1234yf and HF is extracted from the top of a distillation column, while HFO-1234yf is obtained from the bottom of the distillation column. This process requires a larger distillation column because it is necessary to extract a large amount of HFO-1234yf together with HF from the top of the column. Moreover, even when employing a process in which the azeotropic mixture is recycled, the circulation of a large amount of an HFO-1234yf and HF mixture requires that large equipment be used in the process, leading to increases in equipment and operating costs. Further, for example, PTL 4 discloses a process in which a mixture of HF and HFO-1234yf is subjected to azeotropic distillation, the outflow is liquefied by cooling, followed by liquid-liquid separation, and each liquid is distilled, thereby separating HFO-1234yf and HF. In this process, it is necessary to repeat heating a large amount of separated product, followed by cooling and heating again in the separation step, resulting in a large level of energy consumption and increasing the operating cost.

CITATION LIST

Patent Literature

PTL 1: U.S. Pat. No. 2,996,555
PTL 2: WO 2008/002499 A1
PTL 3: WO 2009/105512 A1
PTL 4: WO 2008/024508 A1

SUMMARY OF INVENTION

Technical Problem

An object of the present invention is to provide a method for purifying HFO-1234yf by removing HF from a mixture of HFO-1234yf and HF under simple and economically advantageous conditions.

Solution to Problem

The present inventors conducted extensive research on a method for purifying HFO-1234yf by removing HF from a mixture containing HFO-1234yf and HF. As a result, the inventors found that HFO-1234yf and HF can be purified and separated by adding a specific extractant to a mixture of HFO-1234yf and HF, and performing extractive distillation, thereby concentrating HF in the extractant phase side, while concentrating HFO-1234yf in the gas phase side.

Specifically, an extractant having higher compatibility with HF than with HFO-1234yf is used to perform extractive distillation under conditions in which the relative volatility $\alpha$ of HFO-1234yf to HF is larger than 1. Thereby, a larger proportion of HFO-1234yf can be distributed to the gas phase side, and a larger proportion of HF can be distributed to the extractant phase side.

The relative volatility $\alpha$ is defined by the following formula:

$$\alpha = (y_A/x_A)/(y_B/x_B)$$

on the proviso that a solution at least essentially consisting of a key component A and a key component B (boiling point of component A<boiling point of component B) is in vapor-liquid equilibrium, wherein $x_A$ is the mole fraction of the low-boiling-point component A in the liquid phase, $x_B$ is the mole fraction of the high-boiling-point component B, $y_A$ is the mole fraction of the low-boiling-point component A in the gas phase, when the gas phase is in equilibrium with the liquid phase, and $y_B$ is the mole fraction of the high-boiling-point component B.

The relative volatility $\alpha$ of HFO-1234yf to HF is a relative volatility when component A is HFO-1234yf, and component B is HF in the above formula. Although the relative volatility $\alpha$ may depend on temperature, conditions are determined so that the relative volatility of HFO-1234yf to HF is greater than 1 in the present invention in the temperature range in which extractive distillation is performed.

Further, although the relative volatility $\alpha$ may depend on the liquid composition, conditions are determined so that the relative volatility of HFO-1234yf to HF is greater than 1 in the range of composition ratio of HF, HFO-1234yf, and extractant in which extractive distillation is performed. That is, when extractive distillation is performed using a specific extractant under conditions in which the relative volatility is greater than 1, a larger proportion of HF can be distributed to the extractant side, and a larger proportion of HFO-1234yf can be distributed to the gas phase side. The extractant can be used to carry out the present invention in the range of conditions in which extractive distillation is performed at a relative volatility greater than 1, preferably 30 or more, and more preferably 50 or more.

The extractant to be used in the present invention is at least one member selected from the group consisting of:

(i) alcohols represented by ROH, wherein R is a alkyl group;

(ii) ethers represented by ROR', wherein R and R' are the same or different, and each is a $C_{1-4}$ alkyl group;

(iii) fluoridation alcohols represented by RfOH, wherein Rf is a $C_{1-3}$ fluoroalkyl group;

(iv) ketones represented by RCOR', wherein R and R' are the same or different, and each is a alkyl group;

(v) esters represented by RCOOR', wherein R and R' are the same or different, and each is a $C_{1-4}$ alkyl group;

(vi) polyols represented by R(OH)n, wherein R is a $C_{1-4}$ alkyl group, and n is an integer of 2 to 3; and (vii) ethylene glycols represented by $R^1O(CH_2CH_2O)_nR^2$, wherein $R^1$ and $R^2$ are the same or different, and each is hydrogen or a $C_{1-4}$ alkyl group, and n is an integer of 1 to 3.

Specifically preferred is an extractant comprising at least one member selected from the group consisting of methanol, ethanol, propanol, butanol, isopropanol, 2-methoxyethanol, trifluoroethanol, pentafluoropropanol, tetrafluoropropanol, acetone, methyl acetate, ethyl acetate, propyl acetate, butyl acetate, 1,4-dioxane, 1,3,5-trioxane, dimethyl ether, diethyl ether, diisopropyl ether, and bis(2-methoxymethyl)ether. Particularly among these, at least one of methanol, ethanol, 2-methoxyethanol, pentafluoropropanol, and 1,4-dioxane is significantly preferred because they exhibit a high ability as extractants.

FIG. 1 shows an embodiment for carrying out the present invention.

(1) A mixture comprising HF and HFO-1234yf, and an extractant are supplied to a distillation column A. The mixture is subjected to extractive distillation in the distillation column A, thereby obtaining a fraction F101 (Fraction I), which contains HFO-1234yf and the extractant and has a lower rate of HF to HFO-1234yf than that of the mixture, from the top of the distillation column A, and obtaining a fraction F102 (Fraction II), which has a higher rate of HF to HFO-1234yf than that of the mixture, from the bottom of the distillation column A.

(2) The fraction F102 is supplied to a distillation column B, and distilled in the distillation column B.

(2-1) When the boiling point of the extractant used is higher than that of HF, a fraction F103 (Fraction III), which contains HF and has a higher HF concentration than that of the fraction F102, is obtained from the top of the distillation column B, and a fraction F104 (Fraction IV), which contains the extractant, is obtained from the bottom of the distillation column.

(2-2) When the boiling point of the extractant used is lower than that of HF, a fraction F104 (Fraction III), which contains HF and has a higher HF concentration than that of the fraction F102, is obtained from the bottom of the distillation column B, and a fraction F103 (Fraction IV), which contains the extractant, is obtained from the top of the distillation column.

Here, when the boiling point of the extractant used is higher than that of HF, the fraction F104 (Fraction IV) obtained in process (2-1) may be supplied to the distillation column A as at least a part of the extractant, as shown in FIG. 2. The extractant can thereby be used in a recycling manner.

Moreover, when the boiling point of the extractant used is lower than that of HF, the fraction F103 (Fraction IV) obtained in process (2-2) may be supplied to the distillation column A as at least a part of the extractant, as shown in FIG. 3. The extractant can thereby be used in a recycling manner.

Furthermore, when distillation is carried out in a manner as shown in FIG. 1, FIG. 2, or FIG. 3, HFO-1234yf can be obtained as a fraction F101 (Fraction I) that does not substantially contain HF and an extractant, and HF can be obtained as a fraction F103 or F104 that does not substantially contain HFO-1234yf and an extractant, by controlling the amount of extractant used, and the operating conditions of each distillation column.

Here, the operating conditions of each distillation column include the temperature of a condenser of the top of the distillation column, the temperature of the bottom of the distillation column, the pressure of the distillation column, reflux ratio, etc.

Moreover, HF obtained here can be reused in various reaction starting materials.

The purification method of the present invention can be considered not only as a method for purifying HFO-1234yf, but also as a method for producing HFO-1234yf comprising the step of obtaining, from a mixture comprising HFO-1234yf and HF, a purified product that contains HFO-1234yf and has a lower ratio of HF to HFO-1234yf than that of the mixture.

In the present invention, the mixture of HFO-1234yf and HF to be subjected to purification may be an outflow from any kind of device, such as an outflow from a reactor in which HF-elimination of fluorocarbon is performed, an outflow from a reactor in which fluorination of chlorofluoro hydrocarbon is performed, or an outflow from a reactor combining these; however, the mixture is not limited thereto. Moreover, extractive distillation may be performed by introducing an outflow obtained by once distilling an outflow from such a reactor, or an outflow obtained by liquid-liquid separation of an outflow from such a reactor, into the distillation column A.

Advantageous Effects of Invention

The present invention provides a novel and effective method for purifying HFO-1234yf by removing HF from a mixture of HFO-1234yf and HF.

According to the method of the present invention, the use of extractive distillation allows removal of HF from a mixture of HFO-1234yf and HF, without using sulfuric acid, alkali, water, etc. Thereby, HFO-1234yf can be purified more economically and more safely, and the amount of waste can be reduced compared with methods of removing HF using sulfuric acid, alkali, water, etc.

DESCRIPTION OF EMBODIMENTS

One embodiment of the present invention is described below with reference to drawings.

Figure 1:
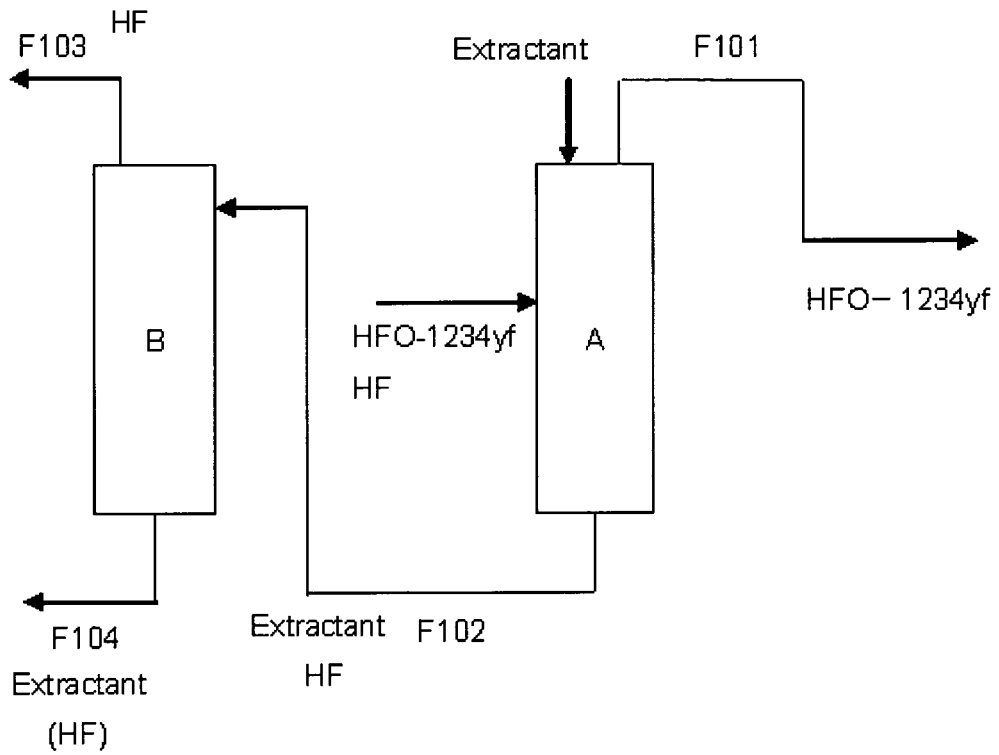
FIG. 1 is a schematic diagram explaining the purification method for HFO-1234yf in one embodiment of the present invention.
Figure 2:
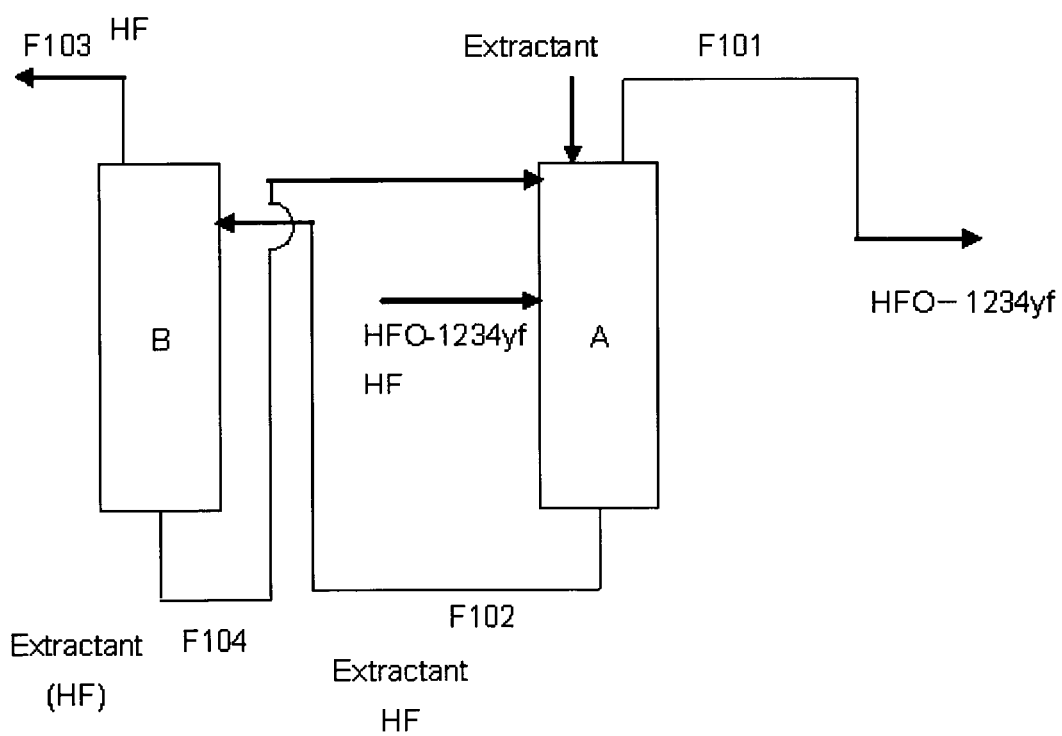
FIG. 2 is a schematic diagram explaining the purification method for HFO-1234yf in another embodiment of the present invention in which an extractant having a boiling point higher than that of HF is used in a recycling manner.
Figure 3:
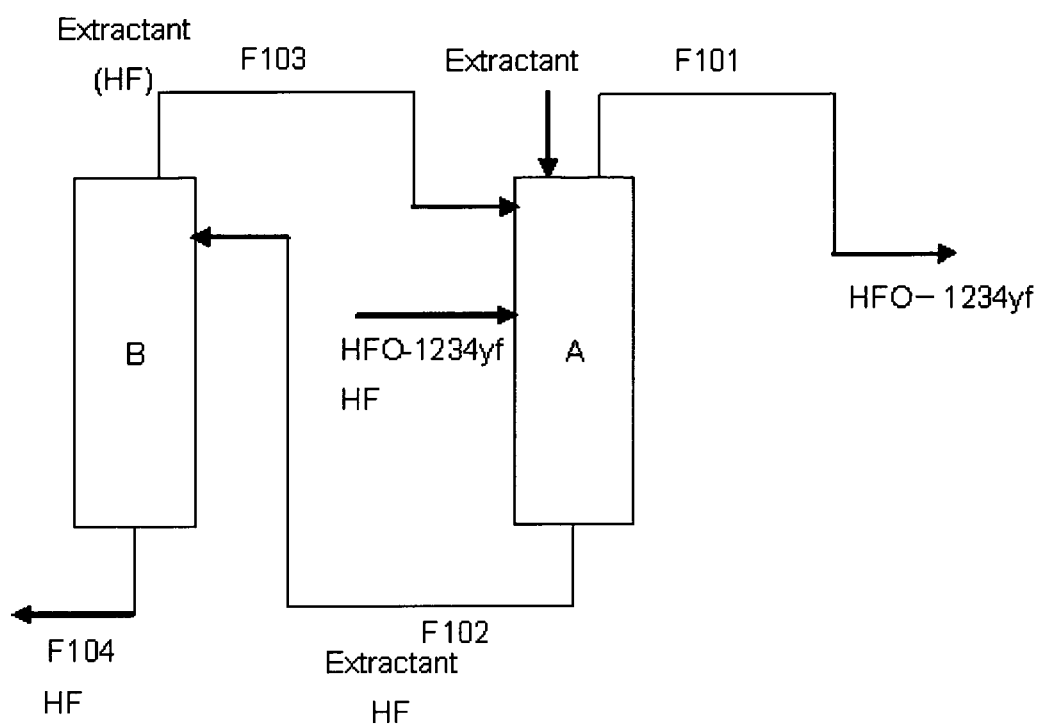
FIG. 3 is a schematic diagram explaining the purification method for HFO-1234yf in another embodiment of the present invention in which an extractant having a boiling point lower than that of HF is used in a recycling manner.

As shown in FIG. 1, a mixture comprising HFO-1234yf and HF is supplied from the middle section of a distillation column A. An example of the mixture is a product obtained by a reaction process in which HFO-1234yf is synthesized by contacting a starting material, i.e., a chlorine compound such as 2-chloro-3,3,3-trifluoropropene (HCFC-1233xf) represented by $CF_3CCl$=$CH_2$ or 2-chloro-1,1,1,2-tetrafluoropropane (HCFC-244bb) represented by $CF_3CClFCH_3$, with HF in the presence of a catalyst in the production process of HFO-1234yf. Another example is an outflow obtained by subjecting the above product to a separation operation, such as distillation, liquid-liquid separation, or membrane separation. Moreover, the mixture comprising HFO-1234yf and HF to be supplied to the distillation column A is, for example, a product obtained by a reaction process in which HFO-1234yf is synthesized by HF-elimination of a starting material, i.e., a fluorine compound such as 1,1,1,2,2-pentafluoropropane (HFC-245cb) represented by $CF_3CF_2CH_3$ or 1,1,1,2,3-pentafluoropropane (HFC-245eb) represented by $CF_3CHFCH_2F$, in the presence of a catalyst or alkali in the production process of HFO-1234yf. Another example is an outflow obtained by subjecting the above product to a separation operation, such as distillation, liquid-liquid separation, or membrane separation. The mixture comprising HFO-1234yf and HF may further contain HCFC-1233xf, HCFC-244bb, HFC-245cb, HFC-245eb, E,Z-1,3,3,3-pentafluoropropene (HFO-1234ze) represented by $CF_3CH$=$CHF$, 3,3,3-trifluoropropene (HFO-1243zf) represented by $CF_3CH$=$CH_2$, 3,3,3-trifluoropropyne represented by $CF_3C$≡$CH$, etc., which are unreacted products, intermediate products, or by-products of the aforementioned processes. Although the proportion of HF to HFO-1234yf is not limited, in a product obtained in the reaction process of synthesis of HFO-1234yf (i.e., a solution before purification), the amount of HF is about 0.01 to 100 mol per mol of HFO-1234yf. Further, in an outflow roughly purified by distillation, the amount of HF is about 0.01 to 10 mol per mol of HFO-1234yf. Moreover, in an outflow highly purified by liquid-liquid separation, membrane separation, or the like, the amount of HF is about 0.01 to 1 mol per mol of HFO-1234yf.

Meanwhile, an extractant is supplied from the top of the distillation column A. The extractant used has a higher compatibility with HF than with HFO-1234yf. An extractant to be used in the present invention is at least one member selected from the following group consisting of:

(i) alcohols represented by ROH, wherein R is a $C_{1-5}$ alkyl group, (ii) ethers represented by ROR', wherein R and R' are the same or different, and each is a $C_{1-4}$ alkyl group, (iii) fluorinated alcohols represented by RfOH, wherein Rf is a $C_{1-3}$ fluoroalkyl group, (iv) ketones represented by RCOR', wherein R and R' are the same or different, and each is a $C_{1-4}$ alkyl group, (v) esters represented by RCOOR', wherein R and R' are the same or different, and each is $C_{1-4}$ alkyl group, (vi) polyols represented by R(OH)n, wherein R is a $C_{1-4}$ alkyl group, and n is an integer of 2 to 3, and (vii) ethylene glycols represented by $R^1O(CH_2CH_2O)_nR^2$, wherein $R^1$ and $R^2$ are the same or different, and each is hydrogen or a $C_{1-4}$ alkyl group, and n is an integer of 1 to 3.

An extractant having a low solubility of HFO-1234yf is more preferably used. Specific examples thereof include methanol, ethanol, propanol, butanol, isopropanol, 2-methoxyethanol, trifluoroethanol, pentafluoropropanol, tetrafluoropropanol, etc. These can be used singly or as a mixture thereof; however, the extractant is not limited thereto.

Moreover, an extractant having a high solubility of HF is preferably used. In terms of chemical properties, higher polarity is more preferable because the solubility of HF becomes higher. Specific examples thereof include methanol, ethanol, propanol, butanol, isopropanol, 2-methoxyethanol, trifluoroethanol, pentafluoropropanol, tetrafluoropropanol, etc. These can be used singly or as a mixture thereof; however, the extractant is not limited thereto.

Furthermore, an extractant having a higher boiling point is preferably used, because the higher the boiling point, the easier the separation from the target product HFO-1234yf (boiling point: −29° C.). An extractant having a boiling point higher than 17° C., which is the boiling point of HF, is more preferably used, because the larger the difference from the boiling point of HF, the easier the separation between HF and extractant. The function of the extractant largely depends on the structure of the compound contained therein. Compounds having similar structures can be expected to exhibit similar extractant functions.

The ratio of extractant (S) to HF (F) (S/F), which depends on the extractant used, is for example, preferably about 1 to 20, and more preferably about 5 to 10 (molar ratio); however, the ratio is not limited thereto.

Then, extractive distillation is carried out in the distillation column A. The pressure at this time may be about 0.1 to 1.3 PMa, the overhead temperature may be about −30 to 30° C., and the bottom temperature may be about 10 to 100° C.; however, these conditions are not limited thereto.

According to the present invention, a mixture containing HFO-1234yf and HF can be subjected to extractive distillation so that HF is concentrated in the extractant phase side, and HFO-1234yf is concentrated in the gas phase side, thereby obtaining an HFO-1234yf distillate in which the concentration ratio of HFO-1234yf to HF is higher than that of the mixture, and an HF distillate in which the concentration ratio of HF to HFO-1234yf is higher than the mixture. It is preferable to control the operating conditions of extractive distillation to remove HF from the mixture, thereby obtaining HFO-1234yf that does not substantially contain HF.

EXAMPLES

The present invention is described in detail below, while showing examples regarding the separation of HFO-1234yf and HF using the present invention.

Example 1

Mixtures of HFO-1234yf and HF, as shown in Table 1 below, were each mixed with an extractant (methanol, diisopropyl ether, or acetone), and the resulting mixtures were maintained at 25.5° C. HFO-1234yf and HF of liquid and gas phases were quantified before and after the extractant was introduced, and the relative volatility α of HFO-1234yf to HF was compared between before and after the introduction of the extractant.

TABLE 1

| Run No. | Type of extractant | Amount | | | Ratio (molar ratio) | | | Relative volatility α | |
|---|---|---|---|---|---|---|---|---|---|
| | | HFO-1234yf (g) | HF (g) | Extractant (g) | HF/ HFO-1234yf | Extractant/ HFO-1234yf | Extractant/ HF | Before introduction of extractant | After introduction of extractant |
| 1 | Methanol | 54.29 | 1.95 | 45.6 | 0.205 | 2.99 | 14.6 | 0.61 | 189.2 |
| 2 | Diisopropyl ether | 48.56 | 1.69 | 128.4 | 0.199 | 2.96 | 14.9 | 0.59 | 37.5 |
| 3 | Acetone | 47.83 | 1.52 | 73.6 | 0.181 | 3.02 | 16.7 | 0.57 | 32.4 |

Run Nos. 1 to 3 had almost the same molar ratios of extractant to HFO-1234yf and almost the same molar ratios of extractant to HF, and the relative volatility α was compared. The results showed that methanol has a higher effect of increasing the relative volatility α of HFO-1234yf to HF than the other extractants. That is, methanol is highly preferred as an extractant for carrying out the present invention.

Here, the relative volatility α of HFO-1234yf to HF is defined by the following formula:

$$\alpha = (y_A/x_A)/(y_B/x_B)$$

wherein $x_A$ is the mole fraction of the low-boiling-point component HFO-1234yf in the liquid phase, $x_B$ is the mole fraction of the high-boiling-point component HF, $y_A$ is the mole fraction of the low-boiling-point component HFO-1234yf in the gas phase that is in equilibrium with the liquid phase, and $y_B$ is the mole fraction of the high-boiling-point component HF.

The invention claimed is:

1. A method for purifying 2,3,3,3-tetrafluoropropene,
    (1) the purification method comprising the step of subjecting a mixture comprising 2,3,3,3-tetrafluoropropene and hydrogen fluoride to extractive distillation in a distillation column A using an extractant, thereby obtaining a fraction I that contains 2,3,3,3-tetrafluoropropene and has a lower ratio of hydrogen fluoride to 2,3,3,3-tetrafluoropropene than the mixture, while obtaining a fraction II that contains hydrogen fluoride and has a lower ratio of 2,3,3,3-tetrafluoropropene to hydrogen fluoride than the mixture;
    (2) the extractant comprising at least one member selected from the group consisting of:
    (i) alcohols represented by ROH, wherein R is a $C_{1-5}$ alkyl group,
    (ii) ethers represented by ROR', wherein R and R' are the same or different, and each is a $C_{1-4}$ alkyl group,
    (iii) fluorinated alcohols represented by RfOH, wherein Rf is a $C_{1-3}$ fluoroalkyl group,
    (iv) ketones represented by RCOR', wherein R and R' are the same or different, and each is a $C_{1-4}$ alkyl group,
    (v) esters represented by RCOOR', wherein R and R' are the same or different, and each is a $C_{1-4}$ alkyl group,
    (vi) polyols represented by R(OH)$_n$, wherein R is a $C_{1-4}$ alkyl group, and n is an integer of 2 to 3, and
    (vii) ethylene glycols represented by $R^1O(CH_2CH_2O)_nR^2$, wherein $R^1$ and $R^2$ are the same or different, and each is hydrogen or a $C_{1-4}$ alkyl group, and n is an integer of 1 to 3.

2. The purification method according to claim 1, wherein the extractant comprises at least one member selected from the group consisting of methanol, ethanol, propanol, butanol, isopropanol, 2-methoxyethanol, dimethyl ether, diethyl ether, diisopropyl ether, trifluoroethanol, pentafluoropropanol, tetrafluoropropanol, acetone, methyl acetate, ethyl acetate, propyl acetate, butyl acetate, 1,4-dioxane, 1,3,5-trioxane, diisopropyl ether, and bis(2-methoxymethyl)ether.

3. The purification method according to claim 1, wherein the extractant has a boiling point higher than that of hydrogen fluoride, the fraction I is obtained from the top of the distillation column A, while the fraction II is obtained from the bottom of the distillation column A, and the method comprises the step of feeding the fraction II to a distillation column B in which the fraction II is distilled, thereby obtaining a fraction III that contains hydrogen fluoride and has a higher ratio of hydrogen fluoride than the fraction II from the top of the distillation column B, while obtaining a fraction IV that contains the extractant from the bottom of the distillation column B.

4. The purification method according to claim 3, wherein the fraction IV is used as at least a part of the extractant used in the distillation column A.

5. The purification method according to claim 1, wherein the extractant has a boiling point lower than hydrogen fluoride, the fraction I is obtained from the top of the distillation column A, while the fraction II is obtained from the bottom of the distillation column A, and the method comprises the step of feeding the fraction II to a distillation column B in which the fraction II is distilled, thereby obtaining a fraction III that contains hydrogen fluoride and has a higher ratio of hydrogen fluoride than the fraction II from the bottom of the distillation column B, while obtaining a fraction IV that contains the extractant from the top of the distillation column B.

6. The purification method according to claim 5, wherein the fraction IV is used as at least a part of the extractant used in the distillation column A.

7. The purification method according to claim 1, wherein the mixture comprises at least one member selected from the group consisting of 2-chloro-3,3,3-trifluoropropene, 2-chloro-1,1,1,2-tetrafluoropropane, 1,1,1,2,2-pentafluoropropane, 1,1,1,2,3-pentafluoropropane, E,Z-1,3,3,3-pentafluoropropene, 3,3,3-trifluoropropene, and 3,3,3-trifluoropropyne.

8. The purification method according to claim 2, wherein the extractant has a boiling point higher than that of hydrogen fluoride, the fraction I is obtained from the top of the distillation column A, while the fraction II is obtained from the bottom of the distillation column A, and the method comprises the step of feeding the fraction II to a distillation column B in which the fraction II is distilled, thereby obtaining a fraction III that contains hydrogen fluoride and has a higher ratio of hydrogen fluoride than the fraction II from the top of the distillation column B, while obtaining a fraction IV that contains the extractant from the bottom of the distillation column B.

9. The purification method according to claim 8, wherein the fraction IV is used as at least a part of the extractant used in the distillation column A.

10. The purification method according to claim 2, wherein the extractant has a boiling point lower than hydrogen fluoride, the fraction I is obtained from the top of the distillation column A, while the fraction II is obtained from the bottom of the distillation column A, and the method comprises the step of feeding the fraction II to a distillation column B in which the fraction II is distilled, thereby obtaining a fraction III that contains hydrogen fluoride and has a higher ratio of hydrogen fluoride than the fraction II from the bottom of the distillation column B, while obtaining a fraction IV that contains the extractant from the top of the distillation column B.

11. The purification method according to claim 10, wherein the fraction IV is used as at least a part of the extractant used in the distillation column A.

12. The purification method according to claim 2, wherein the mixture comprises at least one member selected from the group consisting of 2-chloro-3,3,3-trifluoropropene, 2-chloro-1,1,1,2-tetrafluoropropane, 1,1,1,2,2-pentafluoropropane, 1,1,1,2,3-pentafluoropropane, E,Z-1,3,3,3-pentafluoropropene, 3,3,3-trifluoropropene, and 3,3,3-trifluoropropyne.

13. The purification method according to claim 3, wherein the mixture comprises at least one member selected from the group consisting of 2-chloro-3,3,3-trifluoropropene, 2-chloro-1,1,1,2-tetrafluoropropane, 1,1,1,2,2-pentafluoropropane, 1,1,1,2,3-pentafluoropropane, E,Z-1,3,3,3-pentafluoropropene, 3,3,3-trifluoropropene, and 3,3,3-trifluoropropyne.

14. The purification method according to claim 4, wherein the mixture comprises at least one member selected from the group consisting of 2-chloro-3,3,3-trifluoropropene, 2-chloro-1,1,1,2-tetrafluoropropane, 1,1,1,2,2-pentafluoropropane, 1,1,1,2,3-pentafluoropropane, E,Z-1,3,3,3-pentafluoropropene, 3,3,3-trifluoropropene, and 3,3,3-trifluoropropyne.

15. The purification method according to claim 5, wherein the mixture comprises at least one member selected from the group consisting of 2-chloro-3,3,3-trifluoropropene, 2-chloro-1,1,1,2-tetrafluoropropane, 1,1,1,2,2-pentafluoropropane, 1,1,1,2,3-pentafluoropropane, E,Z-1,3,3,3-pentafluoropropene, 3,3,3-trifluoropropene, and 3,3,3-trifluoropropyne.

16. The purification method according to claim 6, wherein the mixture comprises at least one member selected from the group consisting of 2-chloro-3,3,3-trifluoropropene, 2-chloro-1,1,1,2-tetrafluoropropane, 1,1,1,2,2-pentafluoropropane, 1,1,1,2,3-pentafluoropropane, E,Z-1,3,3,3-pentafluoropropene, 3,3,3-trifluoropropene, and 3,3,3-trifluoropropyne.

17. The purification method according to claim 8, wherein the mixture comprises at least one member selected from the group consisting of 2-chloro-3,3,3-trifluoropropene, 2-chloro-1,1,1,2-tetrafluoropropane, 1,1,1,2,2-pentafluoropropane, 1,1,1,2,3-pentafluoropropane, E,Z-1,3,3,3-pentafluoropropene, 3,3,3-trifluoropropene, and 3,3,3-trifluoropropyne.

18. The purification method according to claim 9, wherein the mixture comprises at least one member selected from the group consisting of 2-chloro-3,3,3-trifluoropropene, 2-chloro-1,1,1,2-tetrafluoropropane, 1,1,1,2,2-pentafluoropropane, 1,1,1,2,3-pentafluoropropane, E,Z-1,3,3,3-pentafluoropropene, 3,3,3-trifluoropropene, and 3,3,3-trifluoropropyne.

19. The purification method according to claim 10, wherein the mixture comprises at least one member selected from the group consisting of 2-chloro-3,3,3-trifluoropropene, 2-chloro-1,1,1,2-tetrafluoropropane, 1,1,1,2,2-pentafluoropropane, 1,1,1,2,3-pentafluoropropane, E,Z-1,3,3,3-pentafluoropropene, 3,3,3-trifluoropropene, and 3,3,3-trifluoropropyne.

20. The purification method according to claim 11, wherein the mixture comprises at least one member selected from the group consisting of 2-chloro-3,3,3-trifluoropropene, 2-chloro-1,1,1,2-tetrafluoropropane, 1,1,1,2,2-pentafluoropropane, 1,1,1,2,3-pentafluoropropane, E,Z-1,3,3,3-pentafluoropropene, 3,3,3-trifluoropropene, and 3,3,3-trifluoropropyne.

* * * * *